United States Patent [19]
Reich et al.

[11] Patent Number: 5,446,378
[45] Date of Patent: Aug. 29, 1995

[54] MAGNETO-OPTIC EDDY CURRENT IMAGING APPARATUS AND METHOD INCLUDING DITHERING THE IMAGE RELATIVE TO THE SENSOR

[75] Inventors: Stanley M. Reich, Jericho; Michael Horn, Setauket, both of N.Y.

[73] Assignee: Grumman Aerospace Corporation, Bethpage, N.Y.

[21] Appl. No.: 167,425

[22] Filed: Dec. 15, 1993

[51] Int. Cl.⁶ ............................................. G01N 21/21
[52] U.S. Cl. ..................................... 324/238; 324/225
[58] Field of Search ............... 324/225, 228, 235, 238; 348/125, 128, 134, 131; 340/551; 356/32-35.5

[56] References Cited

U.S. PATENT DOCUMENTS

| | | | |
|---|---|---|---|
| 4,250,451 | 2/1981 | Slagle | 324/239 |
| 4,523,120 | 6/1985 | Assard et al. | 310/323 |
| 4,625,167 | 11/1986 | Fitzpatrick | 324/235 |
| 4,755,752 | 7/1988 | Fitzpatrick | 324/228 |
| 4,881,813 | 11/1989 | Koo et al. | 324/244 X |
| 4,894,615 | 1/1990 | Mermelstein et al. | 324/244 |
| 5,053,704 | 10/1991 | Fitzpatrick | 324/235 |
| 5,243,278 | 9/1993 | Hulsing, II | 324/173 |

Primary Examiner—Sandra L. O'Shea
Assistant Examiner—Roger C. Phillips
Attorney, Agent, or Firm—Scully, Scott, Murphy & Presser

[57] ABSTRACT

A method of magneto-optic eddy current imaging for detecting defects in a ferrous metal, non-ferrous metal, or non-metallic structure test object uses a sensor, magnetic field system, optical system, a video camera and a display. The method includes canceling undesired background of a two-dimensional magneto-optically generated image of a defect in the test object by dithering the image and processing signals from the video camera in compatibility with the dithering. The image is dithered once per frame of the camera, or at a sub-multiple of the frame of the camera, and the dithering may be accomplished manually or mechanically.

27 Claims, 7 Drawing Sheets

MAGNETO-OPTIC EDDY CURRENT IMAGING APPARATUS AND METHOD INCLUDING DITHERING THE IMAGE RELATIVE TO THE SENSOR

BACKGROUND OF THE INVENTION

The present invention relates to magneto-optic eddy current imaging. More particularly, the invention relates to a magneto-optic eddy current imaging apparatus and method.

Instrumentation has recently been developed which opens up a new area of non-destructive inspection technology known as magneto-optic eddy current imaging. This technology makes it possible to generate a real-time image of defects in both metallic and non-metallic structures. For example, defects, such as fatigue cracks and corrosion in ferrous and non-ferrous metals, or cracks and delamination in non-metallic structures. This class of instrumentation utilizes a sensor having a large Faraday magneto-optic effect (1845). Optically active materials exhibiting this effect will rotate the plane of polarization of polarized light passing through it as a function of the applied, or developed, normal magnetic field. A double pass reflective configuration utilizing a non-magnetic dielectric mirror is known in the art. This is typically the way the magneto-optic crystal is used in an instrument. On each pass of the polarized light through the crystal, regardless of direction, the initial polarization is rotated in the same direction as determined by the magnetic field, thus increasing the sensitivity. In this class of instrument an alternating magnetic field induces a uniform flow of eddy currents into the object which are disrupted in the area of a crack, or other defect. This, in turn, creates secondary magnetic fields normal to the induced eddy currents that flow in the sensor. Since the eddy current is parallel to the plane of the sensor, the magnetic field is normal, or perpendicular to it. These low intensity local magnetic fields cause a local rotation of the plane of polarization of the light passing through the sensor. It is these local rotations of the polarization that cause a spatial image to be formed. The image thus formed is latent until the light is passed through an analyzer which converts the polarization to intensity modulation.

A problem arises, since the class of materials which exhibit a high magneto-optic effect resulting in the production of an image of the normal, or perpendicular, magnetic field perturbed by the crack, or defect, is obscured by a highly visible background. The background results from the magnetic wall domains, which are a fundamental part of the material. One reason for the reduced visibility of the cracks, or defects, is that the aforedescribed class of magnetic materials has many small domains which are visible to the eye. When the image is viewed directly, particularly under magnification, or with the aid of a video camera, the resulting wall-domains give the appearance of cracked paint, or a dry lake bed. The wall domains may resemble small cracks, thus making the detection of such cracks difficult. On the other hand, long cracks will pass through a number of domains, which can cause a distortion in their shape.

The principal object of the invention is to provide magneto-optic eddy current imaging apparatus which functions efficiently, effectively and reliably to produce clear images of defects in a structure test object.

An object of the invention is to provide magneto-optic eddy current imaging apparatus which eliminates the undesired background of a two-dimensional magneto-optically generated image of a defect in a test object.

Another object of the invention is to provide a magneto-optic eddy current imaging method which is efficient, effective and reliable in producing clear images of defects in a structure test object.

Still another object of the invention is to provide a magneto-optic eddy current imaging method which eliminates the undesired background of a two-dimensional magneto-optically generated image of a defect in a test object.

Yet another object of the invention is to provide an apparatus and a method for magneto-optic eddy current imaging which eliminates the undesired background which obscures an indication of defects in a ferrous or non-ferrous metal or non-metallic object and thereby produces a clear image of such defects.

Another object of the invention is to provide an apparatus and a method for magneto-optic eddy current imaging which blanks the magnetic wall domains in the output of a processed video display, thereby reducing and essentially eliminating background interference effects as seen by a viewer, whereby the enhanced image enables the user to detect defects such as, for example, cracks, corrosion and delamination, not previously visible, and enables the attainment of the detection very rapidly.

Still another object of the invention is to provide an apparatus and a method for magneto-optic eddy current imaging which may produce a signal to noise that is, image to background, which is sufficient to permit automatic detection, using pattern recognition techniques, thereby making unmanned monitoring of defects, such as cracks and corrosion, feasible.

SUMMARY OF THE INVENTION

In accordance with the invention, the magneto-optic eddy current imaging apparatus for detecting defects in a ferrous metal, non-ferrous metal, or non-metallic structure test object, has a sensor, a magnetic field means for applying a normal magnetic field to the sensor, an optical means for applying polarized light to the sensor, whereby the sensor rotates the plane of polarization passing through it as a function of the applied magnetic field, a video camera means and a display means. The sensor is positioned between the test object and the video camera means. The magnetic field means induces a uniform flow of eddy currents in the sensor and the test object. The eddy currents are disrupted at defects in the test object, thereby creating secondary magnetic fields normal to the induced eddy currents flowing into the sensor. The low intensity local magnetic fields (i.e., the secondary magnetic fields created) produce a local rotation of the plane of polarization of light from the optical means passing through the sensor and resulting in an image. The display means visually displays a detected defect in the test object as the image. The apparatus comprises a background eliminating means for canceling the undesired background of a two-dimensional magneto-optically generated image of a defect in the test object. The background eliminating means includes a dithering means for dithering the image relative to the sensor and a signal processing means electrically connected between the magnetic field means, optical means, video camera means, and the display means for processing signals from the video camera means after dithering or movement by the dithering means.

The dithering means dithers the image once per frame of the video camera means, or it dithers the image at a sub-multiple of the frame of the video camera means. The dithering means may dither the sensor, or the video camera means and optical means, relative to the test object, in synchronism, or asynchronously with, as the case may be, the frame rate of the video camera means, relative to the test object, in synchronism with the frame rate of the video camera means.

The dithering means may include a manual means, an electro-mechanical means, or a mechanical means for dithering the sensor, the video camera means, and/or the optical system means mechanically. The mechanical, or manual, means includes a translating means and a high pass filter means. The translating means translates the frequency spectrum of the video camera means output signals which represent real defects to a higher frequency region. These real defects appear at the display means as displaced objects. The high pass filter means eliminates background signals, which are in the form of DC signals in the frequency spectrum, from the output signals which represent real defects and are at higher frequencies. The high pass filter means of the mechanical means preferably comprises a digital filter means.

In accordance with the invention, a method of magneto-optic eddy current imaging detects defects in a ferrous metal, non-ferrous metal, or non-metallic structure test object by using a sensor, a magnetic field means, an optical means, a video camera and a display. The method comprises the steps of canceling undesired background signals of a two-dimensional magneto-optically generated image of a defect in the test object by dithering the image and processing signals from the video camera after the dithering.

The image may be dithered once per frame of the video camera, or it may be dithered at a sub-multiple of a frame of the video camera. The sensor, the video camera and optical systems may be dithered, in unison, relative to the test object, in synchronism with the video camera frame rate, or the assembly may be dithered, relative to the test object, asynchronously with the video camera frame rate.

The video camera and optical means may be dithered mechanically. The frequency spectrum of the video camera output signals, which represent real defects, is then translated to a higher frequency region. The real defects appear at the display as displaced objects. Thus, background signals are eliminated from the output signals of the video camera by a high pass filter. Again, the background signals are in the form of DC signals, and are eliminated by filtering out such DC signals. Such elimination can be achieved by a digital filter.

In accordance with the invention, a method of magneto-optic eddy current imaging for detecting defects in a test object uses a sensor, a magnetic field system, an optical system, a digital signal processor, a video camera and a display. The method comprises the steps of observing and storing, as a first image 1, the position of the two-dimensional field of the video camera frame under the control of the digital signal processor. The sensor is then moved to a new position over a distance far enough to assure a completely new resolvable image. After that, the observation is repeated with the video camera. The field is then stored, as a second image 2, in a different set of memory locations. The periodicity of the step motion being such that there is a minimal dwell time between frames and the rate being such to insure that a complete frame of video information is stored before the assembly is displaced again. Thereafter, the two sequential images 1 and 2, obtained and stored in memory under the control of the digital signal processor, are digitally subtracted one horizontal line at a time, in effect, point by point, thereby providing the digital signal processing equivalent of a high pass filter which passes the higher frequency components corresponding to the dithered signals which indicate real defects.

BRIEF DESCRIPTION OF THE DRAWINGS

Other objects and features of the present invention will become apparent from the following detailed description considered in connection with the accompanying drawings which discloses embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
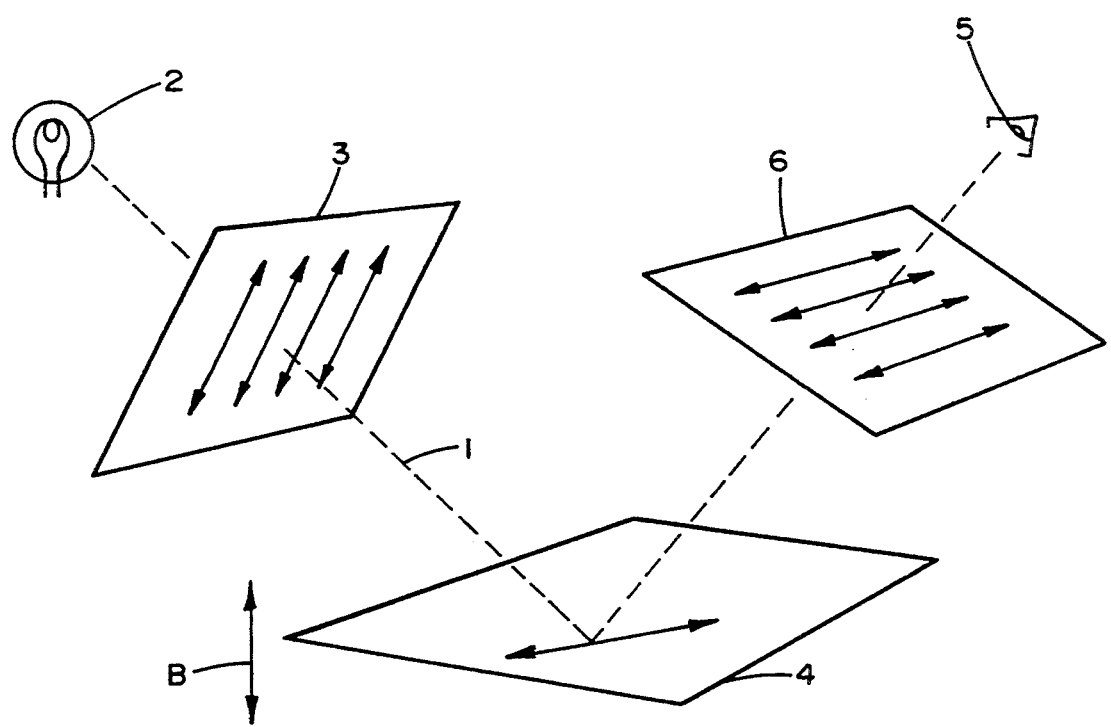
FIG. 1 is a schematic diagram illustrating the Faraday magneto-optic effect in reflective crystal.

FIG. 1 illustrates the Faraday magneto-optic effect in reflective crystal, as hereinbefore described. Polarized light 1 from light source 2 and polarizer 3, of any suitable known type, is reflected by dielectric reflective crystal surface 4. The crystal is in a normal applied magnetic field B and its dielectric coating results in a double pass through said crystal. This increases the rotational sensitivity by a factor of 2 and results in light of rotated polarization appearing to a viewer 5 on an analyzer 6.

Figure 2:
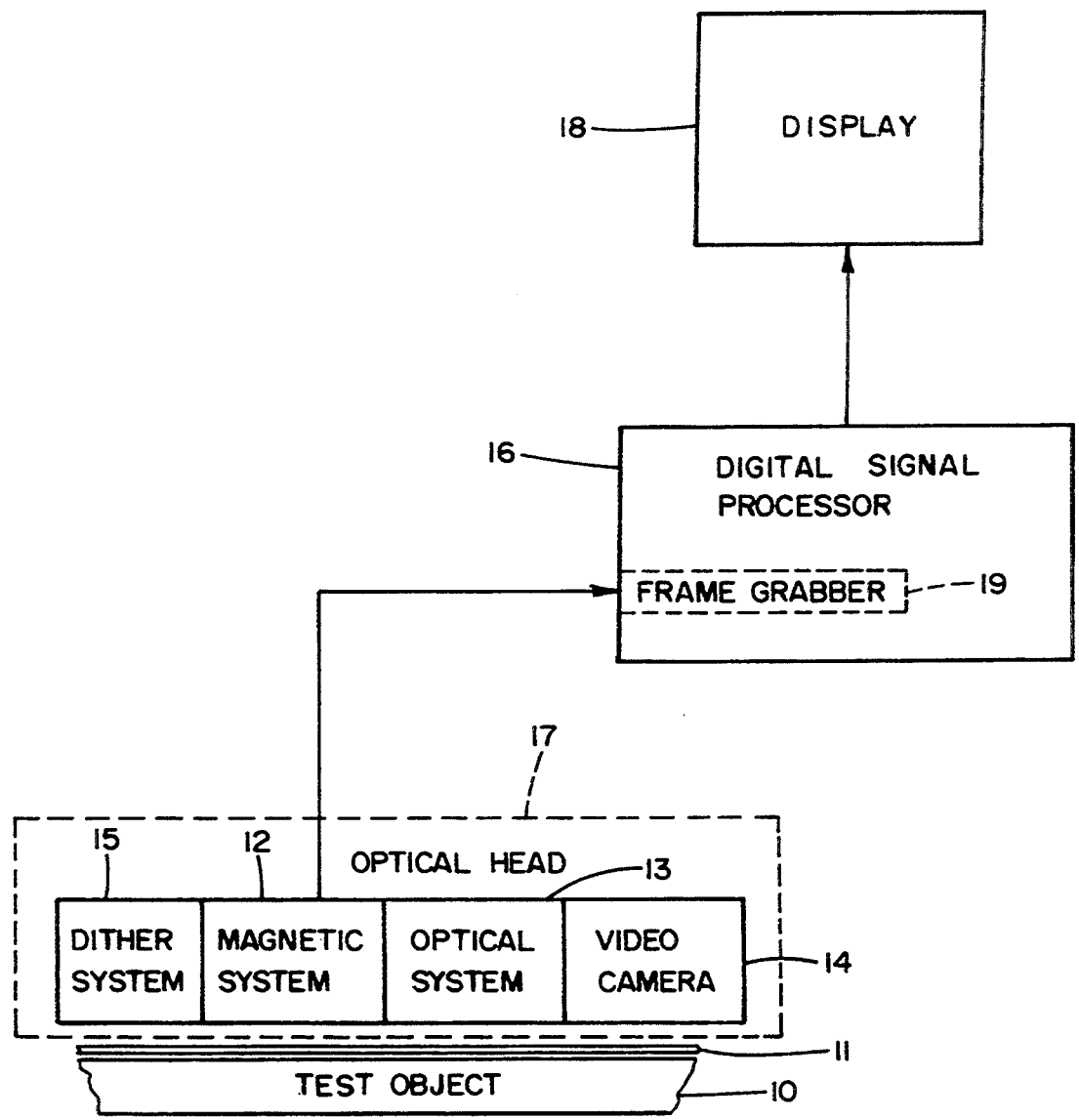
FIG. 2 is a block diagram of an embodiment of the magneto-optic eddy current imaging apparatus of the invention.

FIG. 2 is a block diagram of an embodiment of the magneto-optic eddy current imaging apparatus of the invention for detecting defects in a ferrous metal, a non-ferrous metal and a non-metallic structure test object 10. The apparatus has a sensor 11 of any suitable known type, and a magnetic field system 12 of any suitable known type, for applying a normal magnetic field to said sensor. An optical system 13, of any suitable known type, applies polarized light to sensor 11, whereby sensor 11 rotates the plane of polarization passing through it as a function of the applied magnetic field. A video camera 14, of any suitable known type, is included in the apparatus and sensor 11 is positioned between test object 10 and said video camera 14.

The magnetic field produced by magnetic field system 12 induces a uniform flow of eddy currents in sensor 11 and test object 10. The eddy currents are disrupted at defects in the test object 10, thereby creating secondary magnetic fields normal to the induced eddy currents flowing in sensor 11. The low intensity local magnetic fields (i.e., the secondary magnetic fields created) produce a local rotation of the plane of polarization of light from optical system 13 passing through sensor 11 and resulting in an image.

In accordance with the invention, undesired background signals of the two-dimensional magneto-optically generated image of a defect in test object 10 is canceled. This is accomplished by dither system 15 which dithers the image relative to sensor 11 and signal processor 16. Preferably a digital signal processor 16 is electrically connected between optical head 17 and display 18. Display 18, of any suitable known type, visually displays a detected defect in test object 10 as the image. Optical head 17 includes magnetic system 12, optical system 13, video camera 14 and dither system 15. Signal processor 16 processes signals from video camera 14 after dithering or movement by the dither system 15.

Broadly, the embodiment of FIG. 2 of the magneto-optic eddy current apparatus of the invention is provided by adding signal processing to a system which also has a signature, or identifying characteristic, impressed upon the desired signal so that it can be uniquely recognized with respect to the background. As hereinbefore described, in the embodiment of FIG. 2, a unique signature, or identification, can be created by dithering, or displacing, or moving, the entire camera assembly with respect to the defect of a crack or corrosion, hereinafter referred to as the signal, in a controlled and repeatable fashion while maintaining the camera stationary with respect to the background created by the magneto-optic properties of sensor, or crystal 11. Dithering or displacing the image with respect to the camera/magneto-optic sensor system creates the unique signature. Combining the process of dithering the field with digital signal processing technology is the equivalent of generating an electrical, or spatial, high pass filter. The digital signal processor 16 comprises any suitable known processor such as, for example, a computer or a PC, and includes a frame grabber 19.

FIGS. 3, 4, 5 and 6 are illustrations of first, second, third and fourth modifications of the embodiment of FIG. 2 for producing a unique signature, or identification, for a defect, or signal, in test object 10. In the embodiment of FIG. 2, dither system 15 dithers or displaces the image once per frame of video camera 14, or at a sub-multiple of the frame of said camera. Sensor 11 may be dithered or displaced. In the first modification of FIG. 3, video camera 14 and optical system 13 are dithered, relative to test object 10, in synchronism with the frame rate of video camera 14. In the second modification of FIG. 4, video camera 14 optics and sensor 11 are dithered or displaced, relative to test object 10, in synchronism with the frame rate of said camera. In the third modification of FIG. 5, the image is dithered in a low inertia, low weight manner by modification of the location of the collimator and video camera 14, so they can remain stationary during the dither process.

Sensor 11 is a bismuth-doped iron garnet crystal, or the equivalent. The dithering is, as hereinbefore mentioned, synchronized with the frame rate of video camera 14 and substantially parallel with the plane of test object 10.

Figure 3:
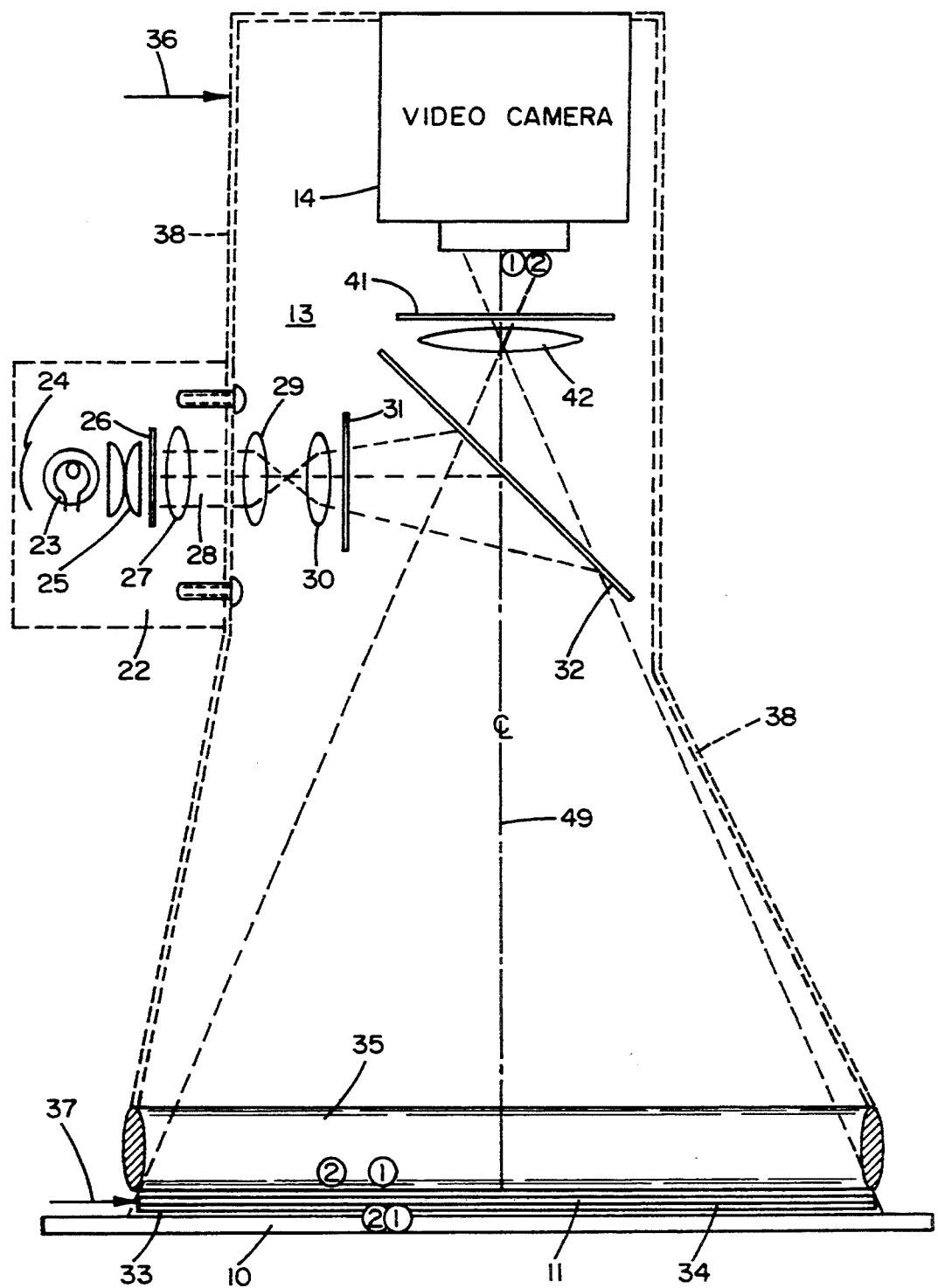
FIG. 3 is a schematic diagram of a first modification of the embodiment of FIG. 2.
Figure 4:
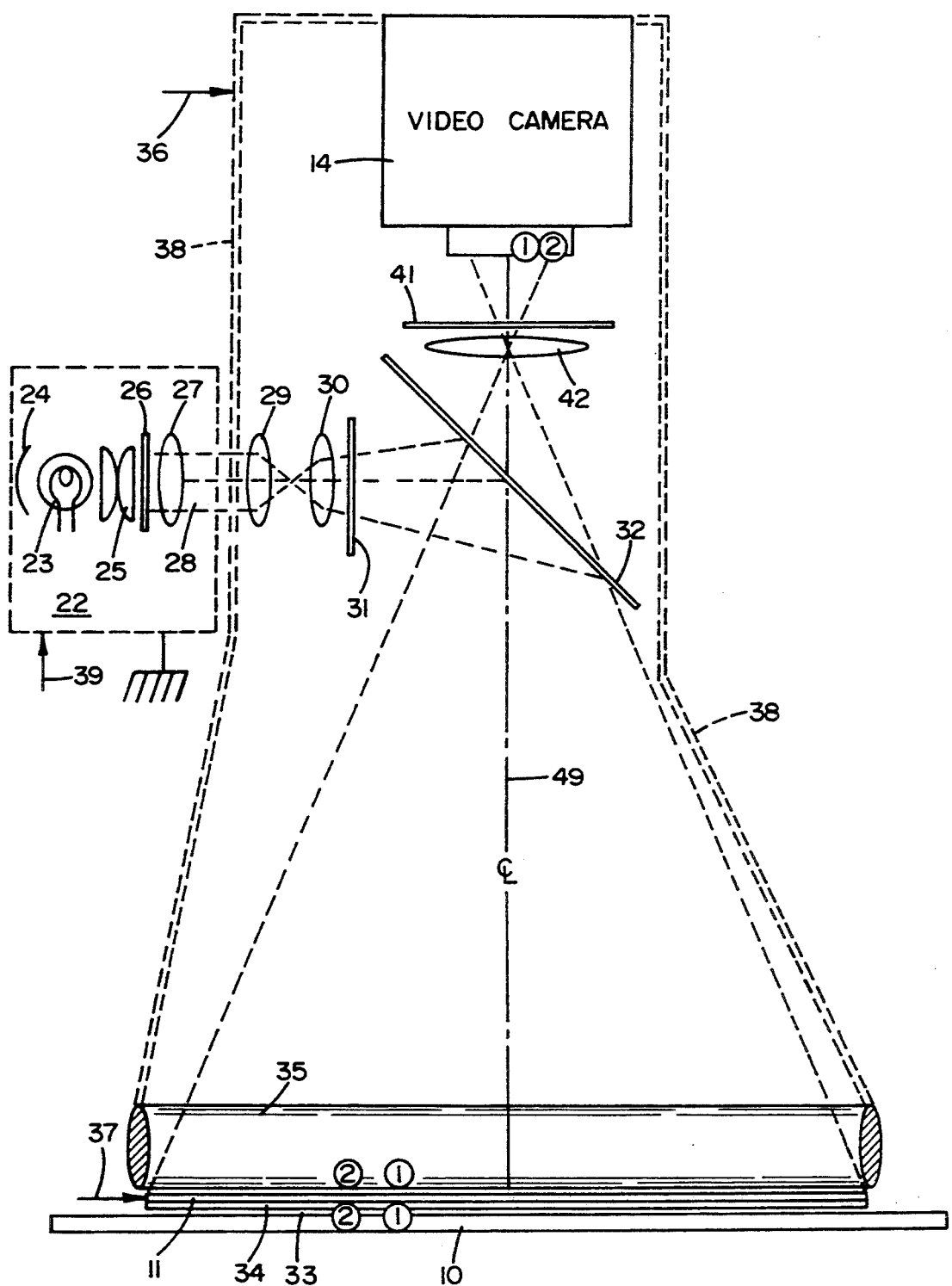
FIG. 4 is a schematic diagram of a second modification of the embodiment of FIG. 2.

In each of FIGS. 3 and 4, optical system 13 includes a lamp assembly 22 having a source of light, or lamp, 23 placed in front of a reflector 24. The light reflected by the reflector 24 is collimated by passage through a condenser lens 25, filter 26 and lens 27. The collimated light 28 produced is output by lamp assembly 22. Collimated light 28 passes through lenses 29 and 30 and a polarizer 31 to a mirror 32 which reflects the polarized light through sensor, or crystal, 11 and a gap 33 to test object 10. A dielectric reflector on the lower surface of sensor 11 reflects the light back through sensor crystal 11 to a lens 42, an analyzer 41 and video camera 14. A sheet conductor 34 is positioned in gap 33 between sensor 11 and test object 10 in substantially parallel relationship to the planes of said sensor and said test object, which are substantially parallel. Magnetic system 12 includes a substantially annular bias magnet 35, of which sheet conductor 34 functions as part.

Figure 5:
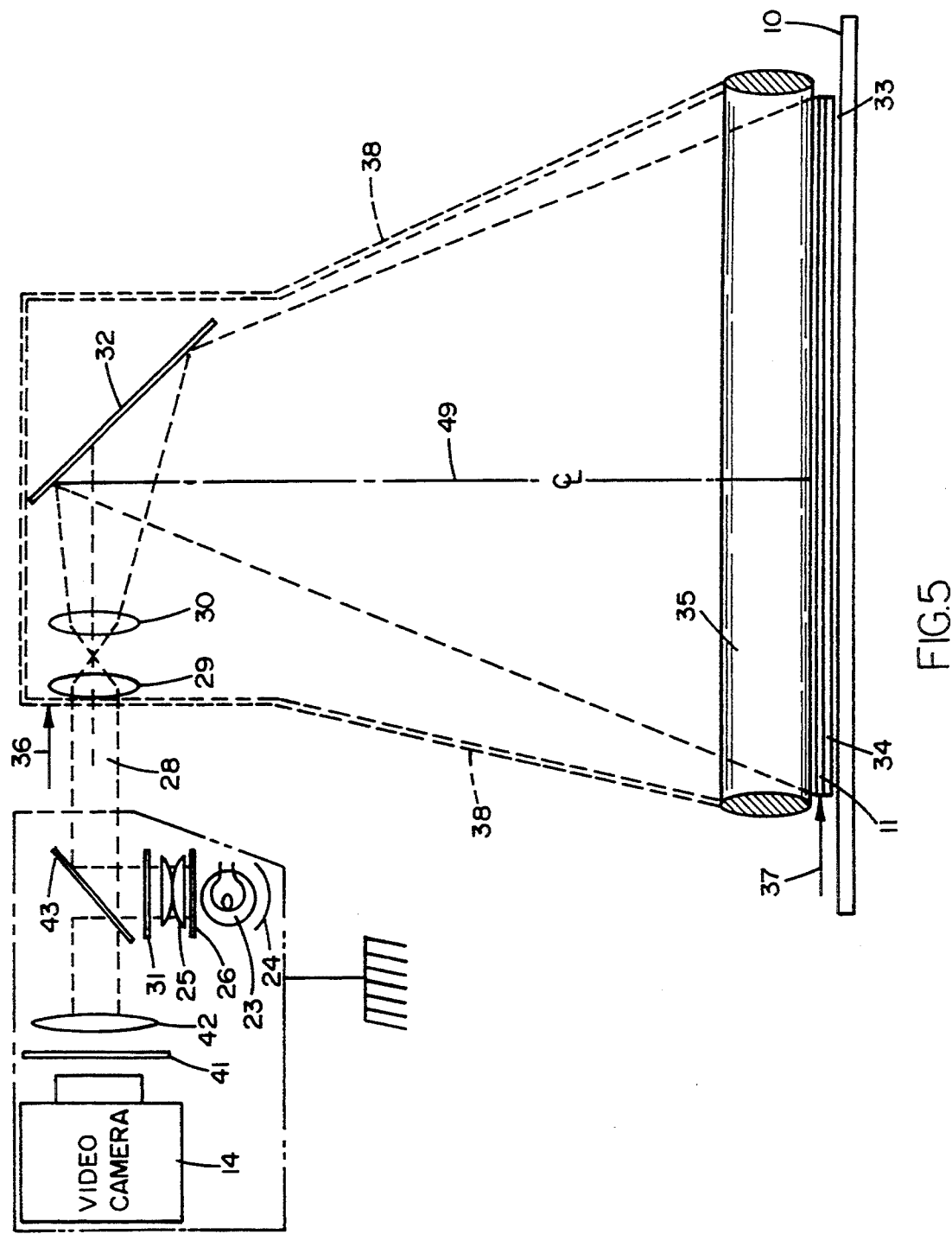
FIG. 5 is a schematic diagram of a third modification of the embodiment of FIG. 2.

In the modification of FIG. 3, the entire video camera 14 and lamp assembly 22 is dithered relative to test object 10, as indicated by dither arrows 36 and 37 operating against frame 38, which frame includes lamp assembly 22 affixed thereto. In the modification of FIG. 4, lamp assembly 22 is separate from frame 38 and remains stationary, as indicated by arrow 39. Only video camera 14, its associated optical system 13, and sensor 11 are dithered relative to test object 10, as indicated by dither arrows 36 and 37. Thus, in the modification of FIG. 4, only the camera assembly is dithered in a direction parallel to test sample 10, in the plane of the section shown and coaxial with the initial collimated beam 28. Because of collimated light beam 28 between the lamp and camera assemblies 22 and 14, respectively, the polarized light generated within lamp assembly 22 illuminates the same field on sensor 11 independent of the moving camera assembly. In order to further reduce the inertia the dither must overcome, video camera 14 is also decoupled from the moving assembly by changing the location of the light assembly 22. This low inertia embodiment is shown in FIG. 5 and could include plastic optics for additional weight and inertia savings. In the highest system, video camera 14 could be moved manually and the operator could initiate the frame grab, or an accelerometer could sense motion and grab successive frames.

In each of FIGS. 3, 4 and 5, analyzer 41 is positioned at the aperture of video camera 14, and lens 42 is interposed between said analyzer and mirror 32 in FIGS. 3 and 4. In FIG. 5, lens 42, beam splitter 43 and lenses 29 and 30 are interposed between analyzer 41 and mirror 32.

Figure 6:
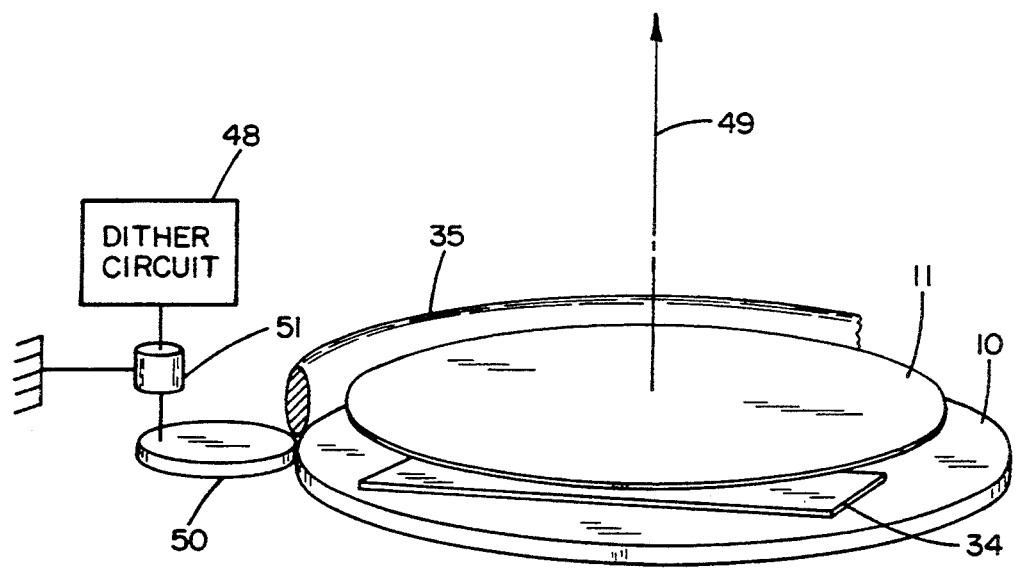
FIG. 6 is a schematic perspective diagram of a fourth modification of the embodiment of FIG. 2.

FIG. 6 shows a preferred embodiment of a mechanism for dithering and is a fourth modification of the embodiment of FIG. 2. In the modification of FIG. 6, dither system 15 of FIG. 2 is driven or energized by a dither circuit 48. The electrical input for circuit 48 is synchronized with the frame rate of video camera 14 and is controlled by digital signal processor 16 (FIG. 2). In FIG. 6, dither system 15 is mechanical and test object 10 is rotated about its axis 49 by an eccentric drive consisting of a cam 50 rotated by electric motor 51 driven by dither circuit 48. Test object 10 is rotatably mounted by any suitable known means, such as, for example, ball or air bearings, or other low friction material. Motor 51 is rigidly mounted. In the actual embodiment, the dither generator would be held stationary relative to test object 10, which could be large. The relative motion would not change.

Figure 7:
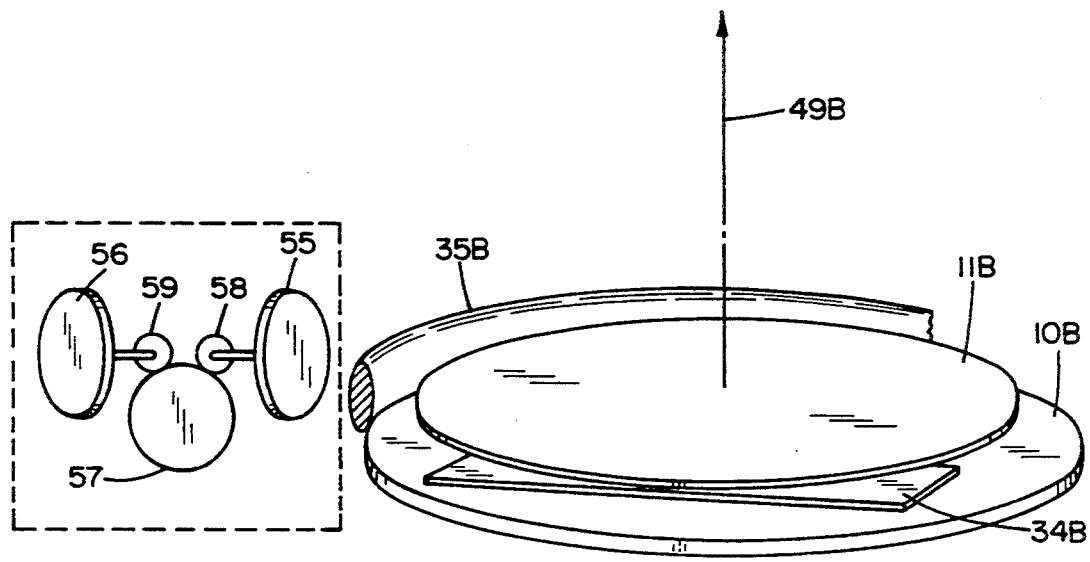
FIG. 7 is a schematic perspective diagram of a fifth modification of the embodiment of FIG. 2.

FIG. 7 is a fifth modification of the embodiment of FIG. 2, wherein a mouse or other motion indicator is used to indicate a position change of the eddy current camera. In the modification of FIG. 7, wherein a manual displacement can be used to locate, or generate, the position of the first frame one and the second frame two, the input can be from an encoder rolling with and attached to the camera.

A manual position shift of the eddy current camera can be detected by a rotary or linear encoder, preferably digital, to measure the displacement of video camera 14. The encoders can be so located on the camera assembly as to monitor relative X and Y orthoginal displacements. The vector sum and absolute position change is computed either in hardware, or software, as the application may require. A computer mouse may be used, as shown in FIG. 7, to input the position information and a resident software program to compute the absolute displacement, as well as provide an indication that a proper displacement has been generated. The instrumentation can be arranged such that the background cancellation function could be manually actuated by a button on the camera handle, or set to automatically occur after a given displacement. Additionally, if an insufficient manual displacement occurs then a warning indication can be added to the display.

The advantage of this method is that no change to the mechanical or electro-optical parts of the existing camera need be made. The system can be stand-alone if a separate video monitor is employed along with the controlling computer and its monitor. All of the electronics can be built into a single package, if so desired.

In FIG. 7, X-encoder 55 and Y-encoder 56 of any suitable known type have motion transferred to them via roller 57. Pick up wheels 58 and 59 are coupled to and rotate coaxially with the X-encoder and the Y-encoder respectively. These components are in a mouse type encoder 60 affixed to the video camera 14 housing. The remaining components of FIG. 7, 10B, 11B, 34B, 35B and 49B are the same as their counterparts of FIG. 6.

Figure 8:
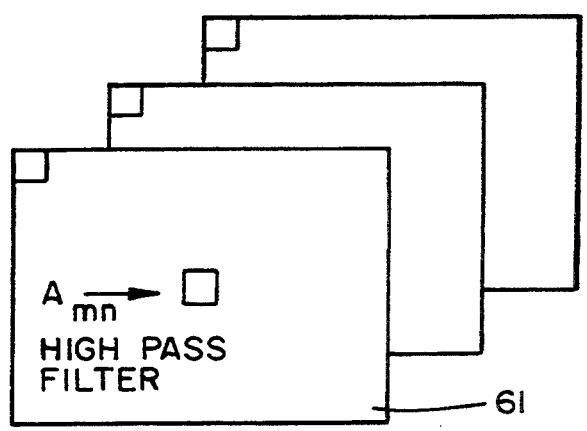
FIG. 8 is a block diagram of a digital high pass filter.
Figure 9:
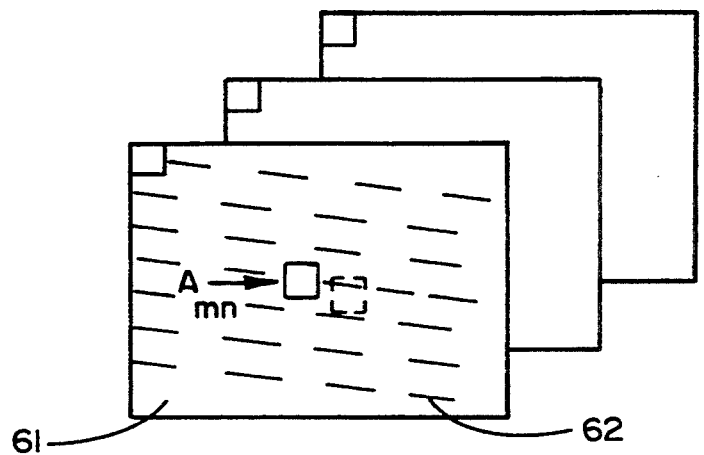
FIG. 9 is a block diagram of the filter of FIG. 8 illustrating the raster.
Figure 10:
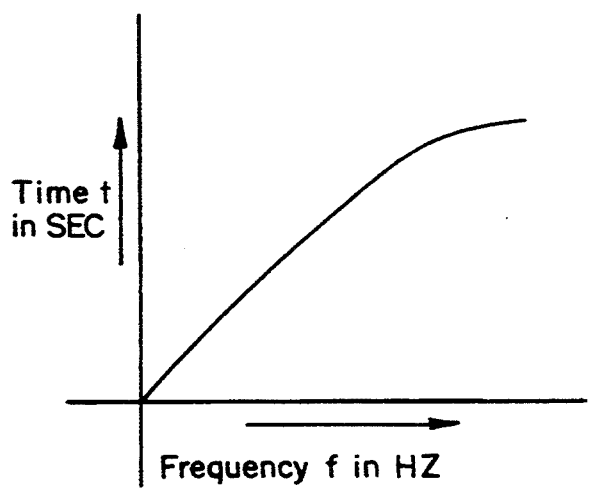
FIG. 10 is a graphical presentation of the frequency output of the filter of FIGS. 8 and 9.

Dither operation, or processing of dithered video camera frames, is based upon a mechanical dither, as shown in FIG. 6. The frequency spectrum of the video camera output signals representing real defects are translated to a higher frequency region. The real defects 1 and 2, shown in FIGS. 3 and 4, appear at display 18 as displaced objects. A high pass filter 61, digital or analog, is then used to eliminate background signals, which are DC signals in the frequency spectrum, from the output signals which represent real defects and are at higher frequencies (FIGS. 8 to 10). Digital filtering lends the additional flexibility of dynamic tuning, or variations in tuning during the taking of a measurement, to optimize results.

In a discrete dither motion system, the sensor sub-system, which is essentially lamp assembly 22, is held in a fixed position for the time it takes to scan a vertical frame of video camera information. A complete frame is defined herein as a fully interfaced or non-interfaced number of horizontal scan lines. The words "vertical" and "horizontal" are historical words defining the two-dimensional field. This unique position of the field is observed and stored in the memory associated with, and under the control of, digital signal processor 16, or other digital subtractor, and is hereinafter referred to as a first image 1.

After dither system 15, under the control of digital signal processor 16, or other timing mechanism, moves magneto-optic sensor 11 of FIGS. 3, 4, or 5 to a new position via the apparatus of FIG. 6, or similar type apparatus, covering a distance far enough to assure a completely new resolvable image, the observation is repeated with video camera 14. The field is stored in a different set of memory locations and is hereinafter referred to as a second image 2. The processing algorithm for a point by point subtraction of the image at location 2 by the original image at location 1 is $$A_{mn} = \frac{1}{2}[a_{mn}(k) - a_{mn}(k-1)]$$

where
A is the result of digital subtraction of frame 1 from 2
a is the coefficient of pixel at location m,n
m is the coordinate of pixel being stored
n is coordinate of pixel being stored
k is the location, or time of frame k The path of the dither with respect to the pixel being canceled and raster 62 are shown in FIG. 9. The motion could occur in a continuous fashion, depending upon the processing approach used. The periodicity of the step motion is such that there is a minimal dwell time between frames and the rate is such to ensure that a complete frame of video information is stored before the assembly is displaced again. The two sequential images 1 and 2, obtained and stored in memory, are then digitally subtracted under the control of digital signal processor 16, one horizontal line at a time, or, in effect, point by point. This is the digital signal processing equivalent of a high pass filter which passes the higher frequency components corresponding to the dithered signal which indicate the real defects such as, for example, cracks or corrosion.

In a subsequent process, the resulting image having two cracks for each original is processed into a single enhanced image and is displayed on a monitor.

FIG. 10 is a graphical presentation of the frequency output of filter 61 of FIGS. 8 and 9. In FIG. 10, the abscissa represents the frequency "f" in Hz and the ordinate represents the time "t" in seconds. The curve of FIG. 10 is indicative of sin $\pi f$.

The method of magneto-optic eddy current imaging of the invention for detecting defects in a ferrous metal, non-ferrous metal, or non-metallic structure test object uses a sensor, a magnetic field system, an optical system, a video camera and a display. The method comprises the steps of canceling undesired background signals of a two-dimensional magneto-optically generated image of a defect in the test object by dithering, or translating, the image and processing signals from the video camera after the dithering, or translation.

The method further comprises the steps of translating the frequency spectrum of the video camera output signals which represent real defects to a higher frequency region. The real defects appear at the display as displaced objects. Background signals are eliminated, by a high pass filter, from the output signals which represent real defects and are at higher frequencies. The background signals are eliminated by eliminating the DC signals.

The method of magneto-optic eddy current imaging of the invention for detecting defects in a test object uses a sensor, a magnetic field system, an optical system, a digital signal processor, a video camera and a display. The method comprises the steps of observing and storing, as image 1, the position of the two-dimensional field of the video camera frame under the control of the digital signal processor. The sensor is then moved to a new position over a distance far enough to assure a completely new resolvable image. After that, the observation is repeated with the video camera. Then, the field is stored, as image 2, in a different set of memory locations, the periodicity of the step motion being such that there is a minimal dwell time between frames and the rate being such to insure that a complete frame of video information is stored before the assembly is displaced again. Thereafter, the two sequential images 1 and 2, obtained and stored in memory under the control of the digital signal processor, are digitally subtracted, one horizontal line at a time, in effect point by point, thereby providing the digital signal processing equivalent of a high pass filter which passes the higher frequency components corresponding to the dithered signals which indicate real defects.

While several embodiments of the present invention have been shown and described, it is to be understood that many changes and modifications may be made thereunto without departing from the spirit and scope of the invention as defined in the appended claims.

What is claimed is:

1. In a magneto-optic eddy current imaging apparatus for detecting defects in one of a ferrous metal, non-ferrous metal and non-metallic structure test object, said apparatus having a sensor, magnetic field means for applying a normal magnetic field to said sensor, optical means for applying polarized light to said sensor, whereby said sensor rotates the plane of polarization passing through it as a function of the applied magnetic field, video camera means, said sensor being positioned between said test object and said video camera means, said magnetic field inducing a uniform flow of eddy currents in said sensor and said test object, said eddy currents being disrupted at defects in said test object, thereby creating secondary magnetic fields normal to the induced eddy currents flowing in said sensor, the low intensity local magnetic fields producing a local rotation of the plane of polarization of light from said optical means passing through said sensor and resulting in an image, the improvement comprising:
background eliminating means for canceling undesired background of a two-dimensional magneto-optically generated image of a defect in the test object, said background eliminating means including:
(i) dithering means for dithering said image relative to said sensor,
(ii) signal processing means, electrically connected to said video camera means, for processing signals from said video camera means after dithering by said dithering means to eliminate undesired background signals.

2. The apparatus as claimed in claim 1, wherein said dithering means dithers said image once per frame of said camera means.

3. The apparatus as claimed in claim 1, wherein said dithering means dithers said image at a sub-multiple of the frame of said camera means.

4. The apparatus as claimed in claim 1, wherein said dithering means dithers said sensor.

5. The apparatus as claimed in claim 1, wherein said dithering means dithers said video camera means and optical means, relative to said test object, in synchronism with the frame rate of said camera means.

6. The apparatus as claimed in claim 1, wherein said dithering means dithers said video camera means and optical means, relative to said test object, asynchronously with the frame rate of said camera means.

7. The apparatus as claimed in claim 1, wherein said dithering means dithers said video camera means, relative to said test object, in synchronism with the frame rate of said camera means.

8. The apparatus as claimed in claim 2, wherein said dithering means includes manual means for dithering said image manually.

9. The apparatus as claimed in claim 5, wherein said dithering means includes mechanical means for dithering one of said sensor and said video camera means and optical means mechanically.

10. The apparatus as claimed in claim 9, wherein said mechanical means includes translating means for translating the frequency spectrum of said video camera means output signals which represent real defects to a higher frequency region, said real defects appearing at said display means as displaced objects, and high pass filter means for eliminating background signals, which are DC signals in the frequency spectrum, from said output signals which represent real defects and are at higher frequencies.

11. The apparatus as claimed in claim 10, wherein said high pass filter means of said mechanical means comprises digital filter means.

12. The apparatus as claimed in claim 1, further including a display means for visually displaying a detected defect in the test object.

13. A method of magneto-optic eddy current imaging for detecting defects in one of a ferrous metal, non-ferrous metal and non-metallic structure test object by using a sensor, magnetic field means, optical means, and a video camera, said method comprising the steps of:
detecting a first two-dimensional magneto-optically generated image of a test object;
dithering the test object and the video camera with respect to each other;
after the dithering, detecting a second two-dimensional magneto-optically generated image of the test object;
processing signals from the video camera by subtracting the first and second two-dimensional magneto-optically generated images, thereby canceling undesired background signals.

14. The method as claimed in claim 13, wherein the image is dithered once per frame of said camera.

15. The method as claimed in claim 13, wherein the image is dithered at a sub-multiple of the frame of said camera.

16. The method as claimed in claim 13, wherein the sensor is dithered.

17. The method as claimed in claim 13, wherein the sensor, the video camera and the optical means are dithered, in unison, relative to said test object in synchronism with the camera frame rate.

18. The method as claimed in claim 13, wherein the sensor, the video camera and the optical means are dithered, in unison, relative to said test object asynchronously with the camera frame rate.

19. The method as claimed in claim 13, wherein the sensor, the video camera, and the optical means are dithered, in unison, relative to said test object in synchronism with the camera frame rate.

20. The method as claimed in claim 13, wherein the video camera is dithered relative to said test object in synchronism with the camera frame rate.

21. The method as claimed in claim 17, wherein the video camera and optical means are dithered mechanically.

22. The method as claimed in claim 21, further comprising the steps of translating the frequency spectrum of the video camera output signals which represent real defects to a higher frequency region, said real defects appearing at the display as displaced objects, and eliminating background signals by high pass filtering said output signals which represent real defects and which are at higher frequencies.

23. The method as claimed in claim 22, wherein said background signals are eliminated by eliminating DC signals.

24. The method as claimed in claim 22, wherein said background signals are eliminated by digital filter.

25. The method as claimed in claim 13, further including the step of displaying a detected defect in the test object.

26. The method of magneto-optic eddy current imaging for detecting defects in a test object, using a sensor, magnetic field system, optical system, a digital signal processor, and a video camera, said method comprising the steps of observing and storing, as a first image, the position of the two-dimensional field of the video camera frame under the control of the digital signal processor;

moving the sensor to a new position over a distance far enough to assure a completely new resolvable image;

repeating the observation with the video camera;

storing the field, as a second image, in a different set of memory locations, the periodicity of the step motion being such that there is a minimal dwell time between frames and the rate being such to insure that a complete frame of video information is stored before the assembly is displaced again; and digitally subtracting the first and second images, obtained and stored in memory under the control of said digital signal processor, one horizontal line at a time, in effect, point by point, thereby providing the digital signal processing equivalent of a high pass filter which passes the higher frequency components corresponding to the dithered signals which indicate real defects.

27. The method as claimed in claim 26, further including the step of displaying a detected defect in the test object.

* * * * *